United States Patent
Kamdar et al.

(10) Patent No.: US 6,409,652 B1
(45) Date of Patent: Jun. 25, 2002

(54) DEVICE AND METHOD FOR DELIVERY OF UNIFORM AND CONTROLLED RADIATION DOSE TO BLOOD VESSELS

(75) Inventors: Kirti P. Kamdar, Sunnyvale; Majid Leonard Riaziat, San Jose, both of CA (US); William K. Wheeler, Austin, TX (US); Raisa Pavlyuchkova, Palo Alto, CA (US)

(73) Assignees: Vascular Architects, Inc., San Jose, CA (US); Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 09/665,729

(22) Filed: Sep. 20, 2000

(51) Int. Cl.[7] .......................... A61N 5/00; A61M 31/00
(52) U.S. Cl. ........................................ 600/3; 604/508
(58) Field of Search ................ 600/3, 1, 2, 4, 600/5, 6, 7, 8; 604/101.05, 53, 96, 102, 103; 606/194

(56) References Cited

U.S. PATENT DOCUMENTS

| | | | | |
|---|---|---|---|---|
| 4,762,130 A | * | 8/1988 | Fogarty et al. | 606/159 |
| 5,059,166 A | * | 10/1991 | Fischell et al. | 600/3 |
| 5,199,939 A | * | 4/1993 | Dake et al. | 600/3 |
| 5,549,554 A | * | 8/1996 | Miraki | 604/101.05 |
| 5,797,948 A | * | 8/1998 | Dunham | 606/194 |
| 5,855,546 A | * | 1/1999 | Hastings et al. | 600/3 |
| 5,865,720 A | * | 2/1999 | Hastings et al. | 600/3 |
| 5,916,143 A | * | 6/1999 | Apple et al. | 600/3 |
| 6,059,713 A | * | 5/2000 | Urick et al. | 600/3 |
| 6,110,097 A | * | 8/2000 | Hastings et al. | 600/3 |

* cited by examiner

Primary Examiner—Eric F. Winakur
Assistant Examiner—Nikita R Veniaminov
(74) Attorney, Agent, or Firm—Pennie & Edmonds LLP

(57) ABSTRACT

The present invention provides a device, system and method for uniformly delivering a radiation dose over the surface area of a stenosed vessel during or after a percutaneous transluminal angioplasty procedure. A helical balloon is inflated in the region to be treated, preferably in contact with the vessel wall, and a radiation source is drawn through the helical coils of the balloon to provide a uniform dosage. Alternatively, the helical balloon is disposed within a cylindrical balloon and the helical balloon containing a radiation source with at least one coil is drawn through the cylindrical balloon.

21 Claims, 4 Drawing Sheets

DEVICE AND METHOD FOR DELIVERY OF UNIFORM AND CONTROLLED RADIATION DOSE TO BLOOD VESSELS

FIELD OF THE INVENTION

The present invention relates to devices and methods for vascular brachytherapy, more particularly vascular brachytherapy in conjunction with percutaneous transluminal angioplasty.

BACKGROUND OF THE INVENTION

Percutaneous transluminal angioplasty (PTA) is a well known technique in which a balloon is located and expanded within a stenosed portion of a vessel. The expansion of the balloon widens the stenosed portion of the vessel to permit more normal blood flow therethrough. PTA is commonly used in, but not limited to, cardiovascular atherectomy procedures. A common problem following PTA is restenosis of the vessel. It is believed that restenosis can be significantly reduced using vascular brachytherapy (VB) following and/or in combination with PTA.

To maximize the benefits of VB, it is desired to apply a measured and uniform dosage over the entire surface area of the treated vessel. Additionally, it is desirable to minimize unwanted radiation exposure of the patient's healthy tissues and to minimize the exposure of medical staff to radiation. Attempts to achieve these goals have met with only limited success.

SUMMARY OF THE INVENTION

An embodiment in accordance with the present invention permits the delivery of a substantially uniform radiation dose to a mammalian lumen. The device includes an inflatable balloon disposed towards the distal end of a catheter tube, a pull wire slidably disposed within the catheter tube, a radiation source connected to a distal end of the pull wire and slidably disposed within the inflatable balloon. In use, the balloon is located within a lumen (e.g. a blood vessel) and inflated such that an outer wall of the balloon contacts the inner wall of the lumen. The radiation source is configured to be approximately adjacent to an internal wall of the inflated balloon. The radiation source is then drawn across the internal wall to provide a substantially uniform and controlled dose of radiation over the entire surface of the internal wall of the lumen. A radiation shield may be provided within the inflatable balloon to shield the radiation source during insertion into the lumen. The shielded radiation source is located within the vessel, unshielded, and then drawn through the inflated balloon as described above. Preferably, the balloon includes a helical balloon to guide the radiation source around the periphery of the vessel wall.

DETAILED DESCRIPTION OF THE PREFERRED EMBODIMENTS

Figure 1:
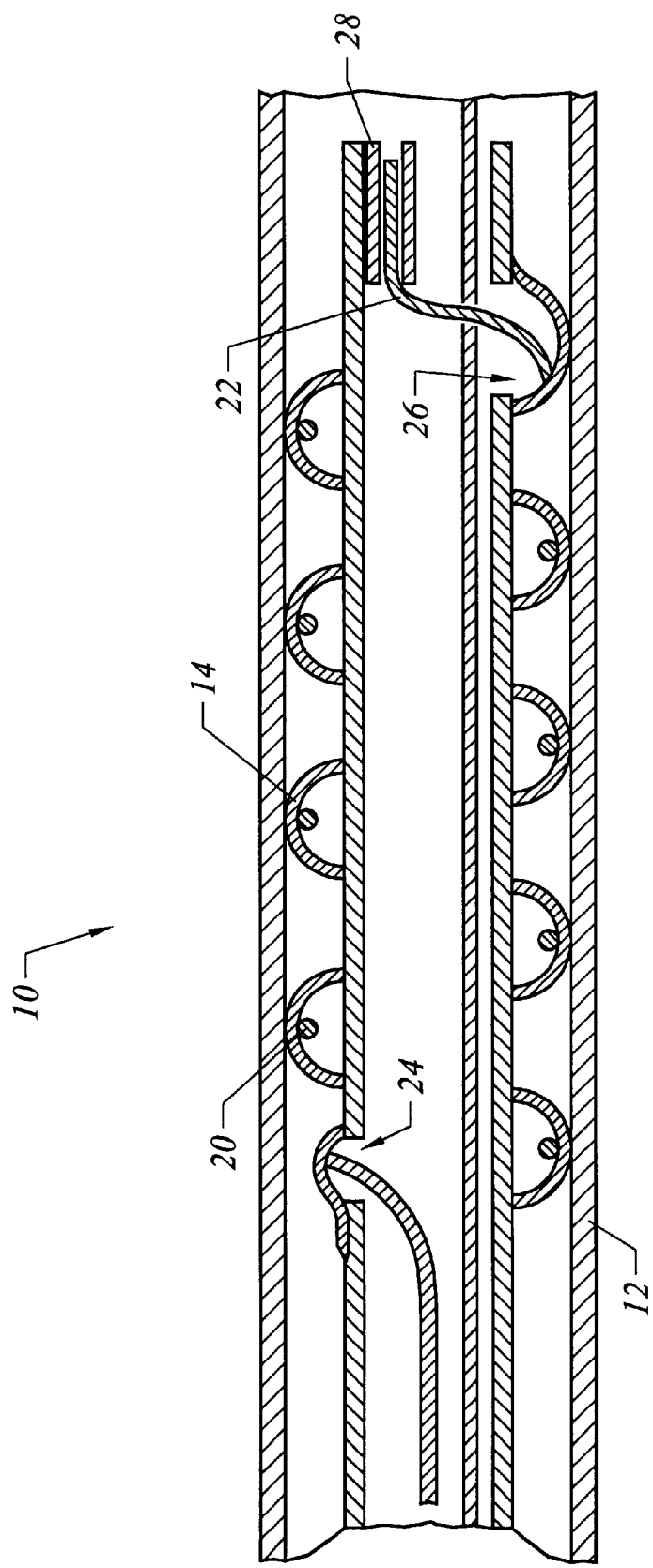
FIG. 1 is a cross-section of a helical balloon catheter for delivering a substantially uniform and controlled radiation dose to a vessel wall in accordance with an embodiment of the present invention.

Referring to FIG. 1, system 10 is capable of uniformly and controllably providing a radiation dose to stenosed vessel wall 12. System 10 has helical balloon 14, catheter shaft 16, pull wire 18, and helical wire 20 with radioactive tip 22. Examples of helical balloons are described in U.S. Pat. No. 4,762,130 entitled CATHETER WITH CORKSCREW-LIKE BALLOON, which is incorporated by reference herein.

Pull wire 18 and helical wire 20 are connected together, and preferably are one single wire. Pull wire 18 extends out of the proximal end (not shown) of catheter shaft 16, thereby permitting medical personnel to manipulate the same, as will be understood by the skilled artisan. Helical wire 20 extends through hole 24 in catheter shaft 16, through the helical turns of helical balloon 14, out of hole 26 in catheter shaft 16, and is connected to and preferably integral with radioactive tip 22. In addition to providing a pathway for helical wire 20 into helical balloon 14, holes 24 and 26 also provide fluid communication between helical balloon 14 and the proximal end of shaft 16 (not shown), and are used to inflate helical balloon 14 within the vessel in a known manner. The skilled artisan will recognize different configurations to enable inflation of helical balloon 14.

Radioactive tip 22 is slidably disposed in shield 28. Radioactive tip 22 must be of a material capable of being made radioactive, either directly or by virtue of a radioactive coating, filling, or paint. Radioactive tip 22 is preferably made from a deformable material, such that when drawn out of shield 28 it substantially returns to its original shape. Preferably, radioactive tip 22 takes a helical shape when withdrawn from shield 28. The skilled artisan will recognize that other shapes for radioactive tip 22 will fall within the scope of the present invention. Such additional shapes include, for example and without limitation, circular, any portion of an arc, or a straight piece bendable into an arc when pulled through the helical turns. The shape and/or material of radioactive tip 22 will cause it to substantially abut against the outer wall of the helical turns as it is drawn therethrough, thereby placing radioactive tip 22 substantially adjacent to vessel wall 12. Material from which radioactive tip 22 may be made includes, for example and without limitation, nitinol wire with a hermetically sealed source therein. Preferably, radioactive tip 22 is made from nitinol wire (approximately 0.018" diameter) with a hermetically sealed β-source therein. Shield 28 is made from material suitable to shield the type of emitter being used, i.e., γ or β.

Additionally, shield 28 may be made from or coated with a material that is radiopaque, permitting its use as a marker for locating the device within the vasculature.

In use, catheter shaft 16 slides over guide wire 30 into a vessel, and radiopaque markers (not shown) are used to locate helical balloon 14 within the treatment region, as will be understood by the skilled artisan. Inflation of helical balloon 14 causes the helical turns thereof to substantially abut against vessel wall 12. Pull wire 18 is used to draw radioactive tip 22 from shield 28, and further to draw radioactive tip 22 through the helical turns at a predetermined velocity.

Figure 4:
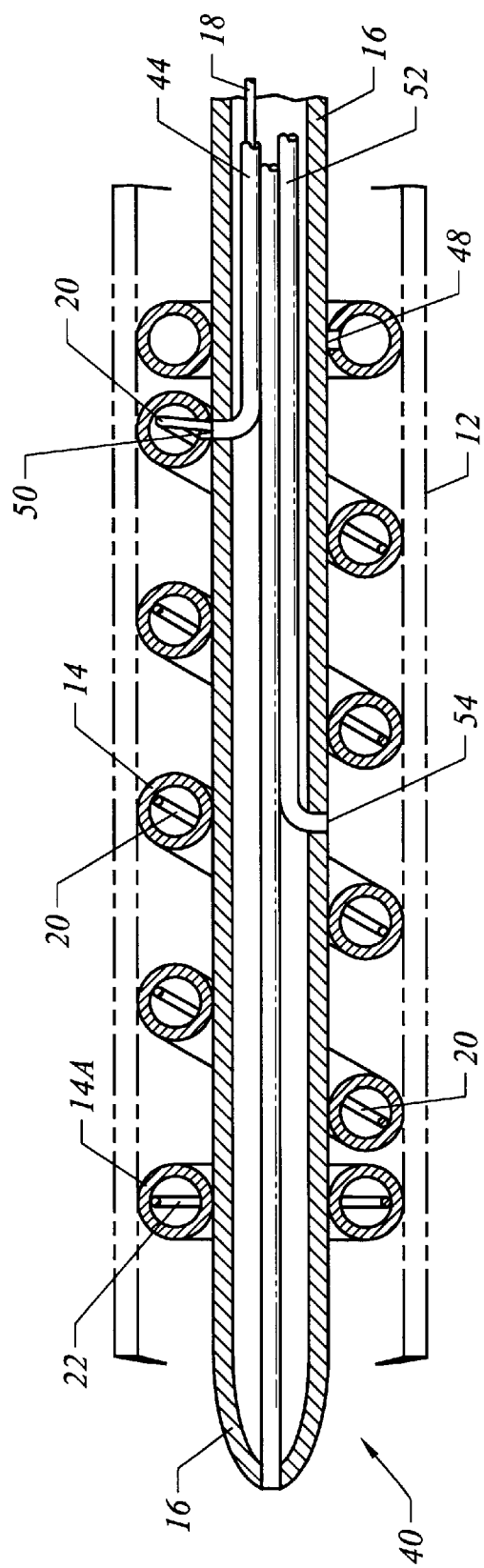
FIG. 4 is a cross-section of a further alternative embodiment of the present invention.

In an alternative embodiment illustrated in FIG. 4, catheter 40 has first coil 14A of helical balloon 14 made of a shielding material such that first coil 14A serves as the shield rather than a separate shield 28 as, for example, in FIG. 1. Catheter 40 also is provided with guide wire lumen 42 and pull wire lumen 44, which isolate those passages from the inflation fluid present within main lumen 46, which communicates with helical balloon 14 through at least one inflation port 48. An appropriate seal may be provided at wire port 50, leading into pull wire lumen 44, in order to prevent leakage of inflation fluid into the pull wire lumen. Thus, helical balloon 14 in may be inflated by introducing a pressurized inflation fluid into main lumen 46 as is known in the art. An optional, separate fluid lumen 52, communicating with the area outside catheter 40 via fluid port 54 may be provided for pressure measurements, additional drug therapies and the like.

Figure 2C:
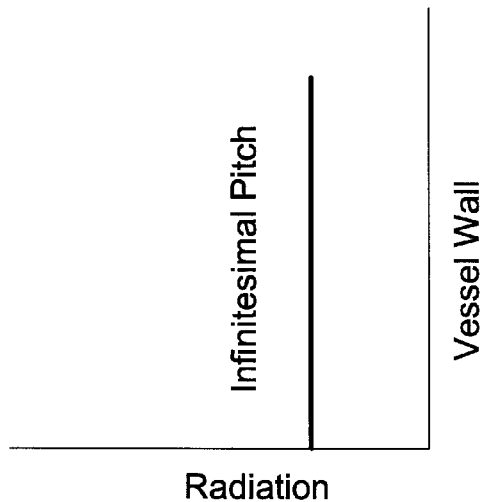
FIGS. 2A–2C provide hypothetical radiation dosage profiles versus longitudinal location on a vessel wall to demonstrate the affect that pitch of the helical balloon has on the uniformity of radiation dosage.
Figure 2B:
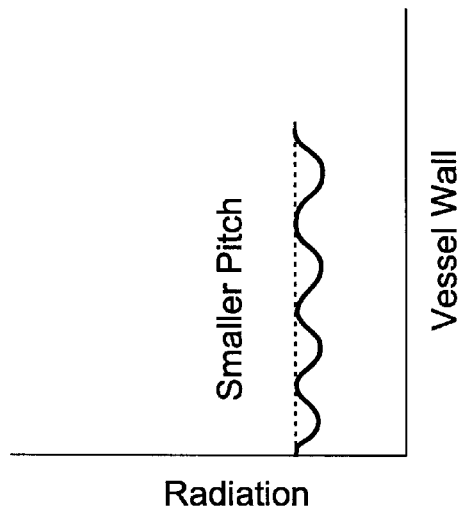
Figure 2A:
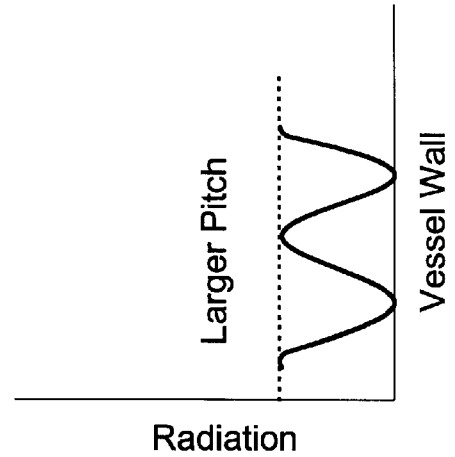

Radioactive tip 22 is substantially adjacent to vessel wall 12 as it is being drawn through the helical turns, thereby significantly reducing fall off of radioactive strength between the source and the vessel wall. Factors that determine dosage are dwell time, as determined by the velocity with which radioactive tip 22 is drawn through the helical turns, and the strength of the radioactive source. The pitch of the helical turns is used to provide a substantially uniform dosage over the entire surface of the vessel. A series of hypothetical plots, shown in FIGS. 2A–C, of radiation profiles versus position along the vessel wall illustrate this point. After radioactive tip 22 has been drawn through helical balloon 14, the highest radiation dosage will be where the tip came closest to the vessel wall and the lowest where the tip is furthest away from the vessel wall. As reflected in FIG. 2A, a relatively large pitch results in a sinusoidal shaped distribution along the length of the vessel. As reflected in FIG. 2B, a smaller pitch results in a more even distribution. As reflected in FIG. 2C, as the pitch becomes hypothetically infinitesimal the profile approaches perfect uniformity. However, as the pitch becomes smaller and smaller it becomes more difficult to pull radioactive tip 22 through the helical turns.

Figure 3:
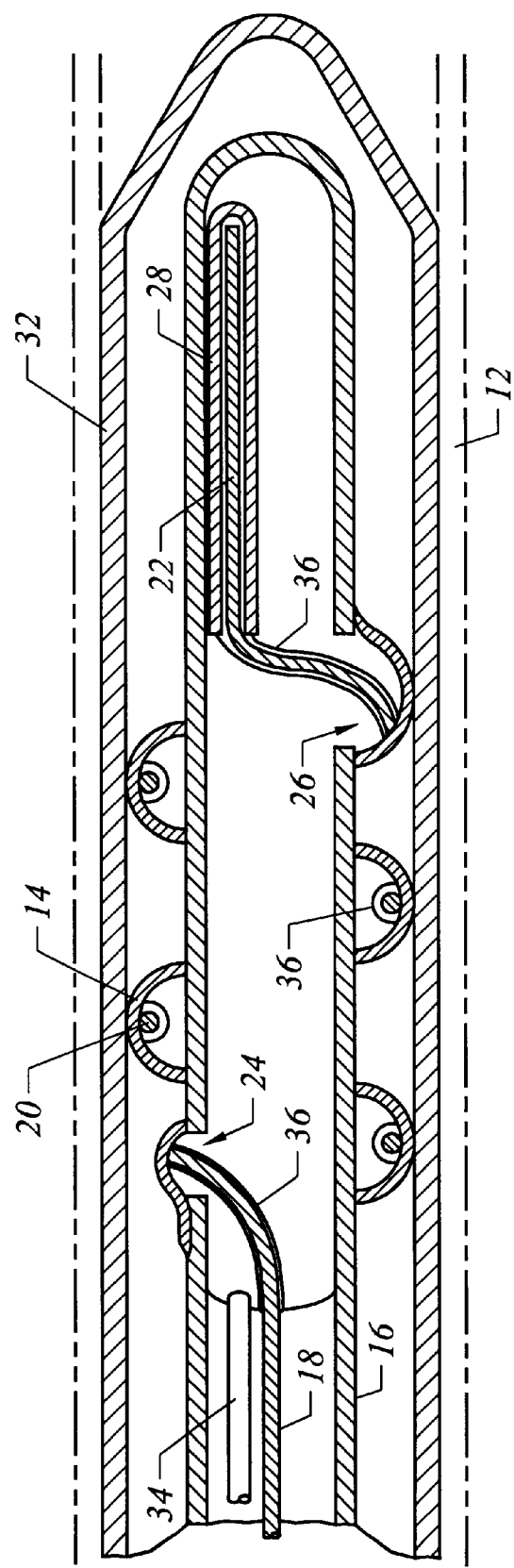
FIG. 3 is a cross-section of a catheter system for delivering a substantially uniform and controlled radiation dose to a vessel wall in accordance with another embodiment of the present invention.

At the limit of pitch equaling zero it may be viewed as pulling a ring of radioactive source across the surface of a cylindrical balloon, which balloon is adjacent the vessel. Referring to FIG. 3, an alternative embodiment slidably disposes a catheter such as described above into substantially cylindrical sheath balloon 32, with the exception that helical balloon 14 may be much shorter in length than the region to be treated and thus shorter than the length of cylindrical balloon 32. Cylindrical balloon 32, when inflated, substantially contacts the vessel wall 12 in the region to be treated. The helical turns, when inflated, substantially contact the inner wall of inflated cylindrical balloon 32. Radioactive tip 22, in this embodiment, has a length approximately equal to at least one helical turn (or any integral number thereof). Rather than pull radioactive tip 22 through the helical turns, it is only drawn into the helical turn(s) such that radioactive tip 12 spans one helical turn or an integral number thereof, which helical turns substantially contact the inner surface of cylindrical balloon 32. Helical balloon 14 is then traversed through cylindrical balloon 32 at a predetermined velocity, such that an even amount of radiation is delivered over the entire surface of the vessel wall. As with the previous embodiment, the radiation source is placed substantially adjacent to the vessel wall being treated.

In the FIG. 3 embodiment, inflation lumen 34 provides inflation fluid to the central void of the distal end wherein it communicates with balloon 14 through openings 24 and 26. Sheath 36 isolates helical wire 20 from the inflation fluid and also helps maintain the wire at the outer periphery of the balloon coils. Shield 28 in this case also has a closed distal end to prevent entry of inflation fluid. In this arrangement, no sliding seals are necessary to isolate the pull wire from the inflation fluid.

By virtue of placing the source substantially adjacent to the target vessel wall, the present invention facilitates the use of a preferred β-emitting source. Shielding of radiation from β-emitters and general exposure risk from β-emitters is much less substantial than that for γ-emitters. Therefore, the ability to effectively use β-emitters provided by the present invention, as well as the ability to shield the radiation source during placement within the vessel greatly increases the ease of performing vascular brachytherapy. For example, medical personnel need not evacuate the room when inserting the device or exposing the patient to the radiation source, and the risk of unwanted radiation exposure to the patient and/or medical staff is significantly reduced. A skilled artisan will nonetheless recognize that γ-emitters may be used without deviating from the scope of the present invention. Preferred β-emitting sources include without limitation $^{90}$Sr-$^{90}$Y, $^{32}$P, or $^{188}$Re. Preferred γ-emitting sources include without limitation $^{192}$Ir, $^{125}$I, or $^{103}$Pd.

In all of the embodiments described herein, the radiation source is removed as quickly as is safe and practicable after radiation treatment of the desired region is completed in order reduce unwanted radiation exposure to the patient. Alternatively, a second radiation shield may be provided, located proximally from the first radiation shield 28, at the opposite end of coiled balloon 14, into which the radiation source may be disposed after the desired dosage is delivered. Alternatively, and particularly, in the embodiment of FIG. 3, the radiation source may be pushed back distally into shield 28. This will significantly reduce or eliminate the risk of unnecessary radiation exposure to the patient during final withdrawal of the device, and permit a more deliberate/careful withdrawal of the device. Although various embodiments of the present invention have been described, the descriptions are intended to be merely illustrative. Thus, it will be apparent to the skilled artisan that modifications may be made to the embodiments as described without departing from the scope of the claims set forth below.

What is claimed is:

1. A radiation delivery system, comprising:
   a catheter comprising a central body member having a distal end portion and an inflatable tubular member wrapped around and secured to the distal end portion of the body member;
   a radiation source slidably disposed within said tubular member; and
   a wire slidably disposed in said inflatable tubular member and attached to said radiation source, said wire for sliding said radiation source through said tubular member for substantially uniform delivery of radiation from said source to a site of interest along the tubular member.

2. The system according to claim 1, wherein said tubular member comprises a helical balloon.

3. The system according to claim 2, further comprising a first shield member disposed within said catheter and receiving said radiation source when in a first position whereby radiation from said source is minimized to facilitate handling and positioning of the catheter.

4. The system according to claim 3, wherein said first shield member comprises a portion of the helical balloon.

5. The system according to claim 3, further comprising a second shield member disposed proximally from said first shield member.

6. The system according to claim 2, wherein said radiation source is disposed at a distal end of said wire, said wire being slidably disposed through said helical balloon.

7. The system according to claim 6, wherein the radiation source comprises the distal end of the wire having a radioactive isotope sealed therewith.

8. The device according to claim 1, wherein said radiation source is β-emitter or γ-emitter.

9. The system according to claim 2, further comprising an outer cylindrical balloon surrounding said catheter, wherein said catheter is slidable within said cylindrical balloon.

10. The device according to claim 1, wherein:
said inflatable tubular member is a helical inflatable balloon with a plurality of helical turns;
said wire having a helical coil at its distal end is slidably disposed within the helical turns of said helical inflatable balloon; and
wherein said radiation source is disposed on a distal tip of said helical coil, whereby withdrawal of said pull wire causes said radiation source to follow the path of the helical turns.

11. The device according to claim 1 further comprising a substantially cylindrical inflatable balloon surrounding at least the distal end portion of the catheter, wherein:
said inflatable tubular member is a helical inflatable balloon with a plurality of helical turns slidably disposed within said substantially cylindrical inflatable balloon such that when said helical inflatable balloon is inflated at least one of the helical turns is approximately adjacent to an interior wall of said cylindrical balloon;
said wire comprises a helical coil at a distal end, the helical coil slidably disposed within the helical turns of said helical balloon; and
said radiation source is disposed on a distal tip of said wire such that said radiation source spans approximately an integral number of helical turns.

12. A device for delivering a substantially uniform radiation dose to a lumen, comprising:
an outer catheter member with an inflatable, substantially cylindrical balloon disposed at a distal end of said member;
an inflatable helical balloon slidably disposed within said substantially cylindrical balloon, said helical balloon having a plurality of helical turns;
a radiation source disposed in at least one helical turn of said helical balloon; and
a wire slidably disposed through the substantially cylindrical balloon and connected to said inflatable helical balloon, whereby sliding said wire moves said inflatable helical balloon through said substantially cylindrical balloon at a predetermined velocity and provides a substantially uniform and controlled dose of radiation to the lumen.

13. The device according to claim 12 further comprising a radiation shield into which said radiation source is slidably disposed.

14. The device according to claim 13, wherein said radiation shield is disposed towards a distal end of said substantially cylindrical balloon.

15. The device according to claim 12, wherein said wire is slidably disposed through said inflatable helical balloon, wherein said radiation source is connected to a distal end of said wire such that said radiation source spans at least one helical turn of said inflatable helical balloon, whereby moving said helical balloon through said substantially cylindrical balloon at a predetermined velocity provides a substantially uniform and controlled dose of radiation to the lumen.

16. A method for delivering a substantially uniform radiation dose to a lumen wall, comprising:
locating an inflatable balloon in the lumen;
placing a radioactive source within said inflatable balloon;
inflating said inflatable balloon, wherein an external wall of the inflated balloon substantially abuts the lumen wall, and wherein said radioactive source substantially abuts an internal wall of the inflated balloon; and
drawing said radioactive source along the internal wall of the inflated balloon such that a substantially uniform radiation dose is delivered to the lumen wall.

17. The method according to claim 16, wherein the placing step takes place before the locating step.

18. The method according to claim 16, wherein said placing step includes slidably disposing the radioactive source in a radioactive shield, said shield being disposed in said inflatable balloon.

19. The method according to claim 16, wherein the shape of the inflatable balloon is substantially cylindrical.

20. The method according to claim 16, wherein said inflatable balloon is a helical inflatable balloon.

21. A method for delivering a substantially uniform radiation dose to a lumen wall, comprising:
locating an inflatable, substantially cylindrical balloon in the lumen;
slidably disposing an inflatable helical balloon within said inflatable substantially cylindrical balloon;
placing a radioactive source within said inflatable helical balloon;
inflating said inflatable substantially cylindrical balloon, wherein an external wall of the inflated substantially cylindrical balloon substantially abuts the lumen wall;
inflating said inflatable helical balloon such that an external wall of at least one helical turn of said inflated helical balloon substantially contacts an internal wall of the inflated, substantially cylindrical balloon, wherein said radioactive source substantially abuts an internal wall of an approximately integral number of helical turns of the inflated helical balloon; and
drawing the inflated helical balloon through the inflated substantially cylindrical balloon such that a substantially uniform radiation dose is delivered to the lumen wall.

* * * * *